United States Patent
Chow et al.

(10) Patent No.: US 9,180,139 B2
(45) Date of Patent: Nov. 10, 2015

(54) REGULATOR, PHARMACEUTICAL COMPOSITION ENCOMPASSING THE REGULATOR AND APPLICATION THEREOF

(71) Applicant: NATIONAL CHENG KUNG UNIVERSITY, Tainan (TW)

(72) Inventors: Nan-Haw Chow, Tainan (TW); Hsiao-Sheng Liu, Tainan (TW); Yi-Wen Wang, Tainan (TW); Wen-Tsan Chang, Kaohsiung (TW)

(73) Assignee: National Cheng Kung University, Tainan (TW)

( * ) Notice: Subject to any disclaimer, the term of this patent is extended or adjusted under 35 U.S.C. 154(b) by 32 days.

(21) Appl. No.: 13/893,707

(22) Filed: May 14, 2013

(65) Prior Publication Data

US 2014/0051743 A1    Feb. 20, 2014

(30) Foreign Application Priority Data

May 15, 2012 (TW) .............................. 101117284 A

(51) Int. Cl.

| | |
|---|---|
| *A61K 48/00* | (2006.01) |
| *C07H 21/02* | (2006.01) |
| *C07H 21/04* | (2006.01) |
| *A61K 31/713* | (2006.01) |
| *A61K 31/352* | (2006.01) |
| *A61K 31/7105* | (2006.01) |

(52) U.S. Cl.
CPC ............ *A61K 31/713* (2013.01); *A61K 31/352* (2013.01); *A61K 31/7105* (2013.01)

(58) Field of Classification Search
CPC .............................. A61K 48/00; C12N 15/113
See application file for complete search history.

(56) References Cited

U.S. PATENT DOCUMENTS

| | | |
|---|---|---|
| 2007/0178045 A1 | 8/2007 | Pisano et al. |
| 2010/0196509 A1 | 8/2010 | Braun et al. |
| 2014/0072569 A1* | 3/2014 | Braun et al. ............... 424/139.1 |

FOREIGN PATENT DOCUMENTS

WO    2011063161 A2    5/2011

OTHER PUBLICATIONS

Hsun, "Identification of Novel Molecular Mechinisms of Tumor Suppresor Effect Induced by Soy Isoflavones: Studies on EMP2 and ITM1 Genes," Thesis of Molecular Medicine Institute at National Cheng Kung University, 2004. (Abstract).
Cheng, "The Signaling Events fo EMP2 in Human Cancer Cells," Thesis of Microorganism and Immunology Institute at National Cheng Kung University, 2006. (Abstract).
Morales et al., "FAK Activation and the Role of Epithelial Membrane Protein 2 (EMP2) in Collagen Gel Contraction," Invest. Opthalmol. Vis. Sci. 2009, 50(1):462-9.

\* cited by examiner

*Primary Examiner* — Amy Bowman
(74) *Attorney, Agent, or Firm* — Volpe and Koenig, P.C.

(57) ABSTRACT

The present disclosure is directed to a regulator, a pharmaceutical composition encompassing the regulator and the application thereof. The regulator modulates the expression integrins and/or EMP2, and is employed for treating integrins-associated and/or EMP2-associated diseases.

7 Claims, 10 Drawing Sheets

REGULATOR, PHARMACEUTICAL COMPOSITION ENCOMPASSING THE REGULATOR AND APPLICATION THEREOF

CROSS-REFERENCE TO RELATED APPLICATION AND CLAIM OF PRIORITY

The application claims the benefit of Taiwan Patent Application No. 101117284, filed on May 15, 2012, in the Taiwan Intellectual Property Office, the disclosures of which are incorporated herein in their entirety by reference.

TECHNICAL FIELD

The present disclosure is directed to a regulator, a pharmaceutical composition encompassing the regulator and the application thereof. The regulator regulates the expression of integrins and/or EMP2, and is employed for treating integrins-associated and/or EMP2-associated diseases.

BACKGROUND

Integrins are receptors that can mediate the attachment between a cell and the tissues surrounding thereof, wherein the tissues can be, for example, other cells or the extracellular matrix (ECM). Integrins are also involved in cell signaling and the regulation of cell cycle, shape, and motility. It is now known that activation of integrins allows for bidirectional (outside-in and inside-out) transmission of mechanical and biochemical signals across the plasma membrane, leading to a cooperative regulation of cell functions, including adhesion, migration, growth, and differentiation. Thus, integrins transduce information from the ECM to the cell as well as reveal the status of the cell to the outside so that the cell can make rapid and flexible responses to changes in the environment.

Integrins are transmembrane proteins and have various types, and a cell may have more than one type of integrins on its cell membrane. Specifically, the integrins located on the cell membrane are in the heterodimer form and have an $\alpha$ and a $\beta$ submits which are bound by non-covalent bond. For example, $\alpha V\beta 3$ integrins are formed by an $\alpha V$ and a $\beta 3$ integrin submits.

Integrins on the cell membrane may interact with the epidermal growth factor receptor (EGFR) and therefore influence the growth of cancer cell and cause the resistance to chemotherapy for cancer. Regarding usage of integrins for the research and clinical treatment of cancer, antibody against integrins is applied and antagonize the receptor of integrins so as to inhibit growths of cells, e.g. vascular endothelial cell, in which integrins are highly expressed or cancer cells. On the other hand, expression of integrins family may need to be raised for the repair and/or regeneration of central nervous system. Recently, integrins are taken as the target for the research and clinical treatment of some diseases such as cancer, multiple sclerosis, Crohn's disease, psoriasis, rheumatoid arthritis, acute coronary syndromes, etc.

In 2008, the market of treatment for the above-mentioned diseases was estimated as more than one billion US dollars. Now the products, being available on the market, for the treatment of those diseases include ReoPro (Abciximab) and Tysabri (Natalizumab). ReoPro is a humanized monoclonal antibody that blocks the function of $\beta 3$ integrin and is applied to clinical treatment of percutaneous transluminal coronary angioplasty (PTCA) for unstable angina. Tysabri, a monoclonal antibody, blocks the function of $\alpha 4$ integrin and is used for the monotherapy of relapsing-remitting multiple sclerosis. However, the inhibitor against single integrin molecule, such as $\alpha 4$ or $\beta 3$, does not provide good treatment effects. Moreover, those antibody drugs are expansive, probably induce allergy caused by heterologous protein and may have lost efficacy due to host's immunoreaction.

Furthermore, epithelial membrane protein-2 (EMP2) is a hydrophobic membrane protein and the study and clinical application therefor are limited in the diseases relating to the pathway regulated by female hormones such as endometrial cancer. However, the relations between EMP2 and other proteins or diseases are not clearly demonstrated.

Employing experiments and researches full-heartily and persistently, the applicant finally conceived regulator, pharmaceutical composition encompassing the regulator and application thereof.

SUMMARY

The present disclosure is directed to a regulator, a pharmaceutical composition encompassing the regulator and the application thereof. The regulator regulates the expression of integrins and/or EMP2, and is employed for treating integrins-associated and/or EMP2-associated diseases.

On another aspect, the present disclosure provides a method for treating integrin-associated disease in a mammal, comprising a step of administrating to the mammal an effective amount of a regulator regulating an expression of EMP2.

On another aspect, the present disclosure provides a method for treating EMP2-associated disease in a mammal, comprising a step of administrating to the mammal an effective amount of an inhibitor inhibiting an expression of integrins.

On another aspect, the present disclosure provides a method for treating bladder cancer in a mammal, comprising a step of administrating to the mammal an effective amount of a regulator regulating the expression of EMP2 and integrins.

DETAILED DESCRIPTION

The present disclosure can be fully understood and accomplished by the skilled person according to the following embodiments. However, the practice of present method is not limited to following embodiments.

Figure 1A:
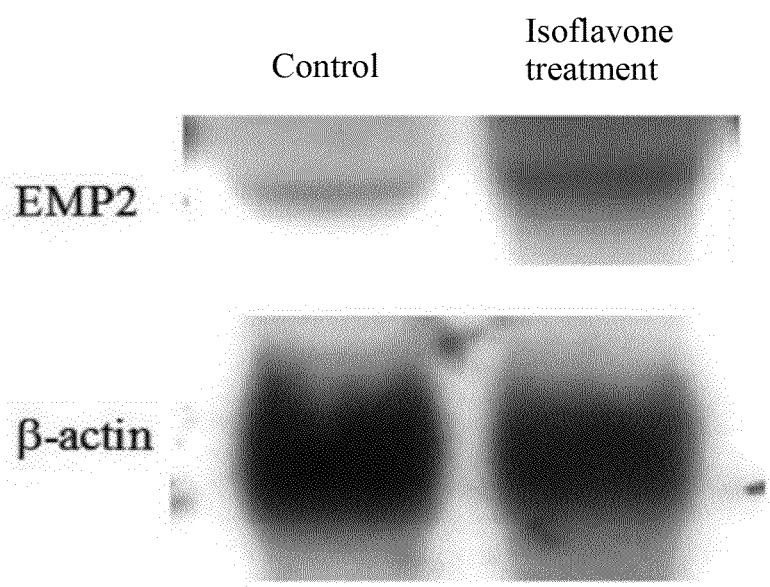
FIG. 1A is a northern blotting figure showing the respective EMP2 mRNA expressions of RT4 bladder cancer cell line treated with genistein (10 μg/mL) for 24 hours (Isoflavone treatment group) or not (Control group).
Figure 1B:
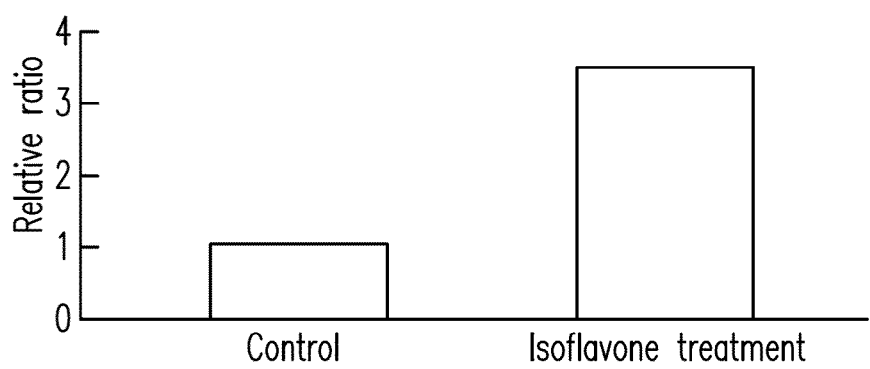
FIG. 1B reveals the ratios of quantifications of EMP2 mRNA expressions of RT4 cell lines in FIG. 1A.

Please refer to FIG. 1A which is a northern blotting figure. FIG. 1A shows the respective EMP2 mRNA expressions of RT4 bladder cancer cell line treated with genistein (10 μg/mL) for 24 hours (Isoflavone treatment group) or not (Control group), wherein β-actin was a housekeeping gene and its mRNA expression was used for normalization. Please further refer to FIG. 1B which reveals the ratios of quantifications of EMP2 mRNA expressions of RT4 cell lines in FIG. 1A, wherein the EMP2 mRNA expression of Control group was defined as 1. As shown in FIGS. 1A and 1B, compared with that of Control group, the EMP2 mRNA expression of RT4 treated with genistein is dramatically higher as up to 3.5 times. That is, genistein, the isoflavone compound, can up-regulate the EMP2 mRNA expression of RT4 cells.

Figure 2:
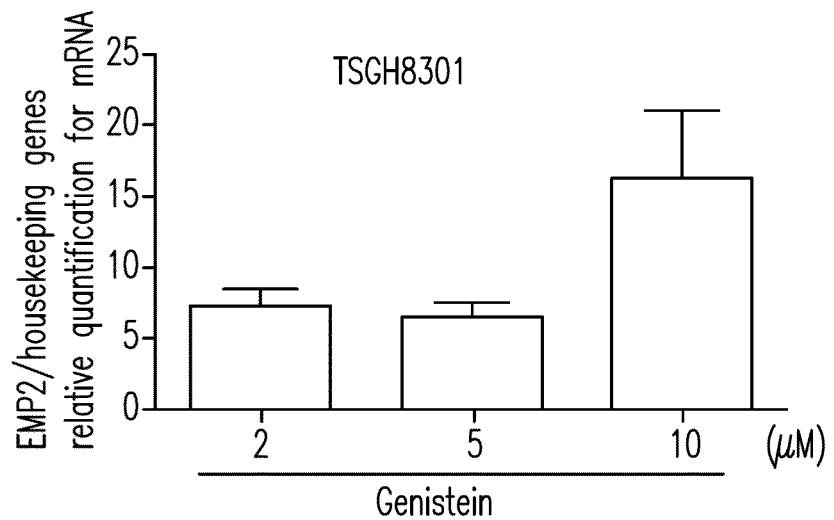
FIG. 2 shows relative quantifications of mRNA expression of EMP2 and housekeeping genes of TSGH8301 human bladder cancer cell line.

Please refer to FIG. 2 which shows relative quantifications of mRNA expressions of EMP2 and housekeeping genes of TSGH8301 human bladder cancer cell lines (P=0.03 by two way ANOVA). TSGH8301 cell lines were initially incubated with mediums containing 2 μM, 5 μM and 10 μM of genistein, respectively, and the respective EMP2 mRNA expressions was measured at sixth day, wherein mRNA expressions of housekeeping gene was taken as the baseline control. With increase of genistein concentration, expression of EMP2 mRNA was increased as shown in FIG. 2. Thus, expression of EMP2 mRNA in TSGH8301 cell line showed a dose-dependent up-regulation by genistein.

Figure 3:
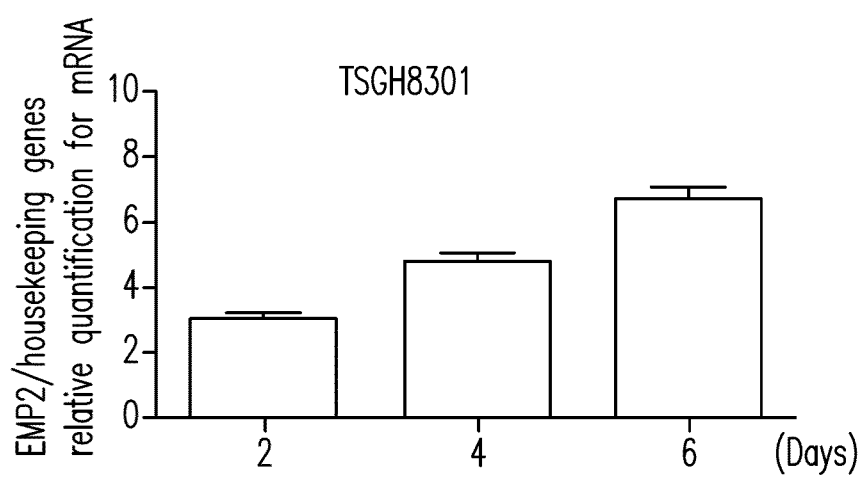
FIG. 3 shows relative quantifications of mRNA expression of EMP2 and housekeeping genes of TSGH8301 cell line.

Please refer to FIG. 3 which shows relative quantifications of mRNA expression of EMP2 and housekeeping genes of TSGH8301 cell lines (P=0.03 by one way ANOVA). TSGH8301 cells were initially incubated with medium containing 15 μM of genistein and EMP2 mRNA expressions were measured at second, fourth and sixth days, respectively, wherein mRNA expressions of housekeeping gene of TSGH8301 cell lines were taken as the baseline control. With increase of incubating durations, EMP2 mRNA expression of TSGH8301 cells incubated with genistein was increased as shown in FIG. 3. Thus, expression of EMP2 mRNA in TSGH8301 cell line shows a time-dependent up-regulation by genistein.

As shown in FIGS. 1A, 1B, 2 and 3, it is known that genistein could be the regulator for up-regulating EMP2 expression.

Figure 4A:
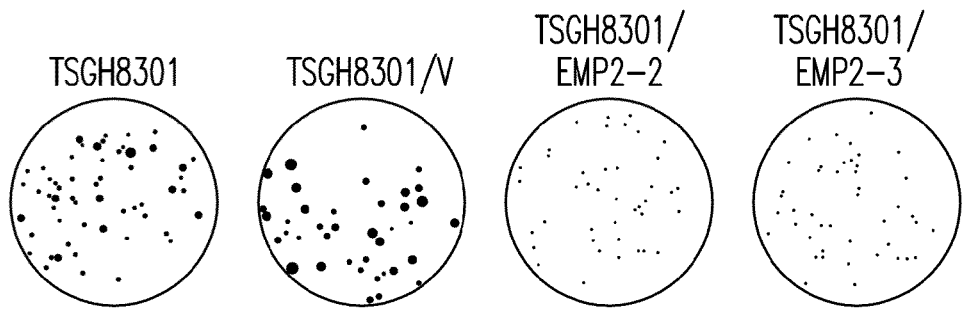
FIG. 4A shows the growth rates of TSGH8301, TSGH8301/V, TSGH8301/EMP2-2 and TSGH8301/EMP2-3 cell lines.
Figure 4B:
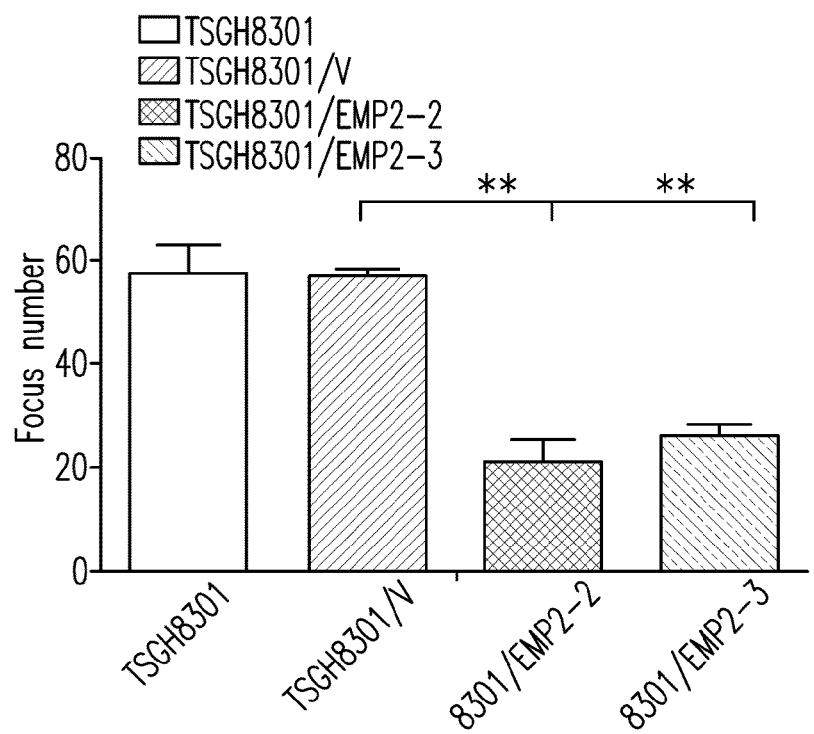
FIG. 4B shows the respective foci numbers of TSGH8301, TSGH8301/V, TSGH8301/EMP2-2 and TSGH8301/EMP2-3 cell lines.

Please refer to FIG. 4A. FIG. 4A shows the growth rate of TSGH8301, TSGH8301/V, TSGH8301/EMP2-2 and TSGH8301/EMP2-3 cell lines, all of which were incubated under the same condition ($2 \times 10^2$ cells plated in 10 cm dish and observed at $14^{th}$ day), wherein foci of these cell lines were stained with Gemisa. TSGH8301/EMP2-2 and TSGH8301/EMP2-3 cell lines were chosen as stable clones for constitutively over-expressing EMP2 by using EMP2-EGFP fusion plasmid, and TSGH8301/V was a clone having EGFP plasmid therein. The foci numbers of TSGH8301, TSGH8301/V, TSGH8301/EMP2-2, and TSGH8301/EMP2-3 cell lines were shown in FIG. 4B (**P<0.01, respectively, paired Student's t test). As shown in FIGS. 4A and 4B, foci formation of both TSGH8301/EMP2 and TSGH8301/EMP2-3 cell lines are significantly lower than that of TSGH8301/V. That is, over-expression of EMP2 indeed significantly inhibits the growth of tumor cells (TSGH8301).

Figure 5:
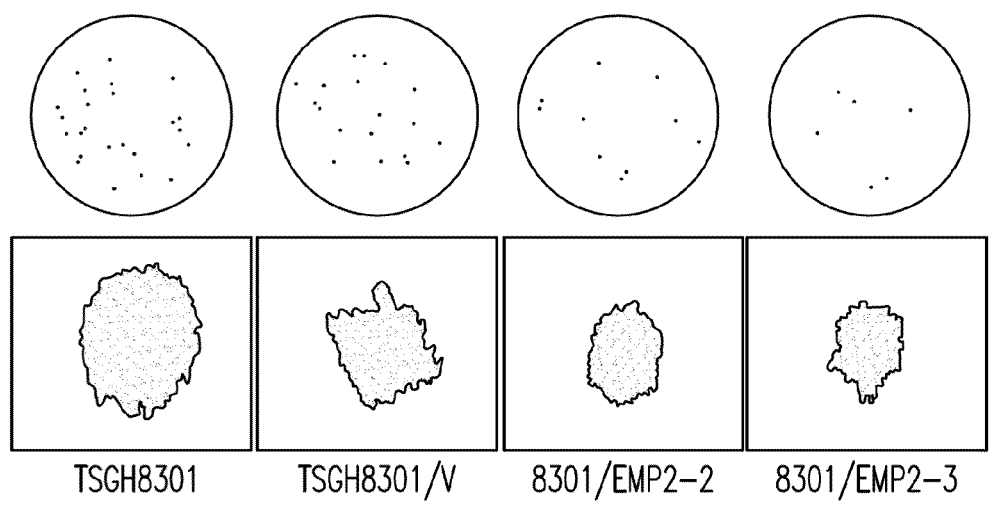
FIG. 5 shows the growth rates of TSGH8301, TSGH8301/V, TSGH8301/EMP2-2 and TSGH8301/EMP2-3 cell lines.

FIG. 5 shows the growth rate of TSGH8301, TSGH8301/V, TSGH8301/EMP2-2 and TSGH8301/EMP2-3 cell lines, all of which were cultured in 0.35% agar containing serum ($3 \times 10^3$ cells plated in six-well trays and observed at $14^{th}$ day) for soft agar assay. The soft agar assay is used for analysis of anchorage-independent growth of cells with the tendency of cancerization. As shown in FIG. 5, TSGH8301/EMP2-2 and TSGH8301/EMP2-3 cell lines have a significantly lower colony number compared with TSGH8301/V cell line (P<0.05, paired Student's t test). Also, the sizes of colony of TSGH8301/EMP2-2 and TSGH8301/EMP2-3 cell lines are smaller than that of TSGH8301/V.

Figure 6:
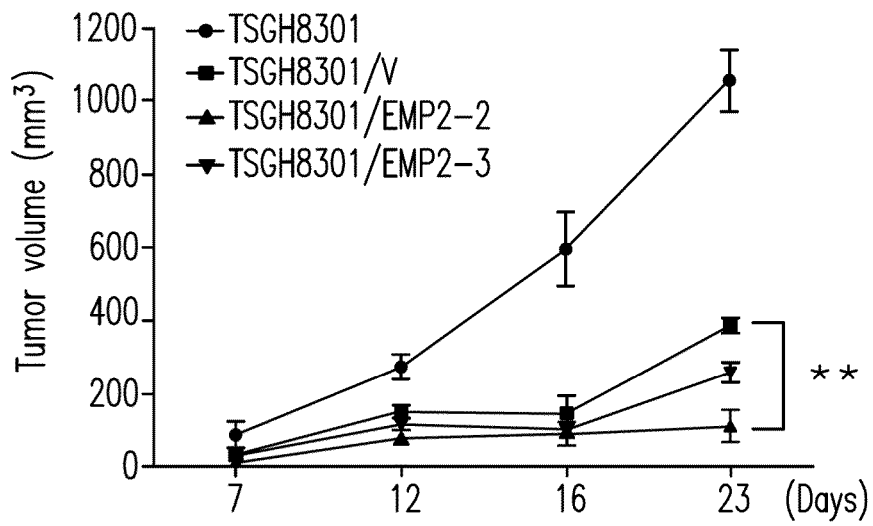
FIG. 6 shows tumor volumes of SCID mice.

To determine the biological significance of EMP2 in vivo, female severe combined immunodeficiency (SCID) mice (5-6 weeks of age) were randomly divided into four groups, and TSGH8301, TSGH8301/V, TSGH8301/EMP2-2 and TSGH8301/EMP2-3 cell lines ($1 \times 10^7$) were inoculated s.c. to the SCID mice, respectively. These SCID mice were fed from 0 day (the date of inoculation) and tumor volume was measured every day until $23^{rd}$ day as shown in FIG. 6. There is no significant difference of tumorigenicity between TSGH8301 and TSGH8301/V cell lines (P>0.05). However, mice inoculated with TSGH8301/EMP2-2 cell line have significantly smaller tumors than those of TSGH8301/V group (**P=0.01) in FIG. 6. Together, up-regulation of EMP2 could inhibit the growth of cancer cell in vivo and in mammals.

Figure 7:
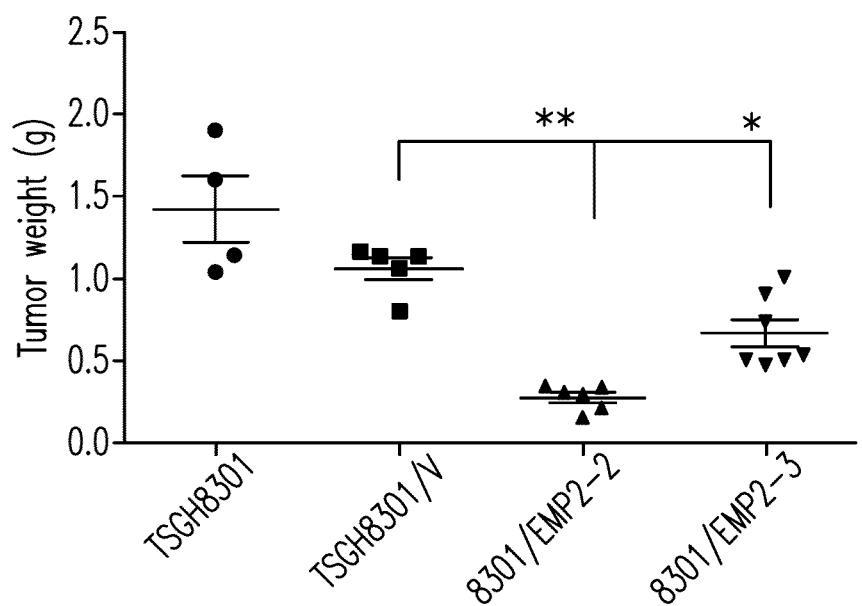
FIG. 7 shows tumor weights of SCID mice.

Above-mentioned mice were continuously fed to $31^{st}$ day and then sacrificed for measuring the tumor weights thereof. The data are shown in FIG. 7. Those mice bearing EMP2 transfectants (inoculated with TSGH8301/EMP2-2 and TSGH8301/EMP2-3 cell lines) have a striking decrease of tumor weight (*P<0.05 and **P<0.01) compared with control mice (inoculated with TSGH8301/V cell line). Again, up-regulation of EMP2 could inhibit the growth of cancer cell in vivo and in mammals.

Results shown in FIGS. 4A, 4B, 5, 6 and 7 suggest a role for EMP2 as the tumor suppressor gene. The growth of cancer cell and development of malignancy are inhibited by up-regulation of EMP2.

Figure 8:
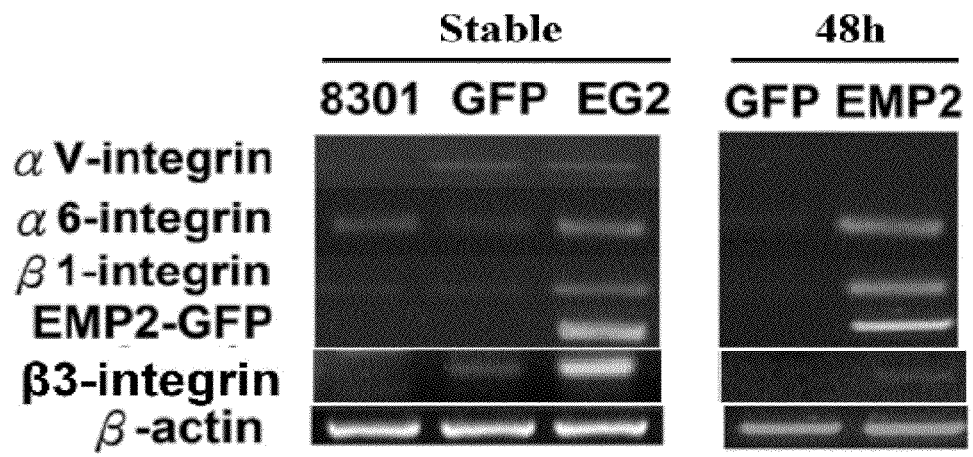
FIG. 8 is a blotting figure showing the results of reverse transcription-polymerase chain reaction.

FIG. 8 shows the results of reverse transcription-polymerase chain reaction (RT-PCR). Specifically, FIG. 8 (left figure) shows the relationship between EMP2 and αV, α6, β1 and β3 integrins at mRNA level in stable cell lines of TSGH8301 (Stable 8301 column), TSGH8301/V (Stable GFP column) and TSGH8301/EMP2-2 (Stable EG2 column), respectively. FIG. 8 (right figure) also shows the relationship between EMP2 and αV, α6, β1 and β3 integrins at mRNA level in transient transfection cell lines containing GFP plasmid (GFP column) and GFP-EMP2 plasmid over-expressing EMP2 (EMP2 column), wherein mRNA of EMP2 and αV, α6, β1 and β3 integrins was harvested at $48^{th}$ hour after transient transfection cell lines being treated with inducer. The β-actin was the housekeeping gene used for normalization.

As shown in FIG. 8, the raise of EMP2 expression will increase the mRNA expressions of αV, α6, β1 and β3 integrins either in stable or transient transfection cell lines. It can be concluded that the regulator and/or factor raising the expression of EMP2 will also raise the expressions of αV, α6, β1 and β3 integrins via the above-mentioned Figs. and descriptions.

Figure 9:
FIG. 9 is a blotting figure showing the results of reverse transcription-polymerase chain reaction.

FIG. 9 shows the relationship between EMP2 and α1 or α5 integrins at mRNA level in stable cell lines of TSGH8301 (8301 column) and TSGH8301/EMP2-2 (8301/EMP2 column) analyzed by RT-PCR. As shown in FIG. 9, EMP2 could up-regulate the mRNA expressions of α1 and α5 integrins in TSGH8301 cell lines. So, regulators and/or factors up-regulate the expression of EMP2 will enhance the expressions of α1 and α5 integrins via above-mentioned Figs. and descriptions.

Figure 10A:
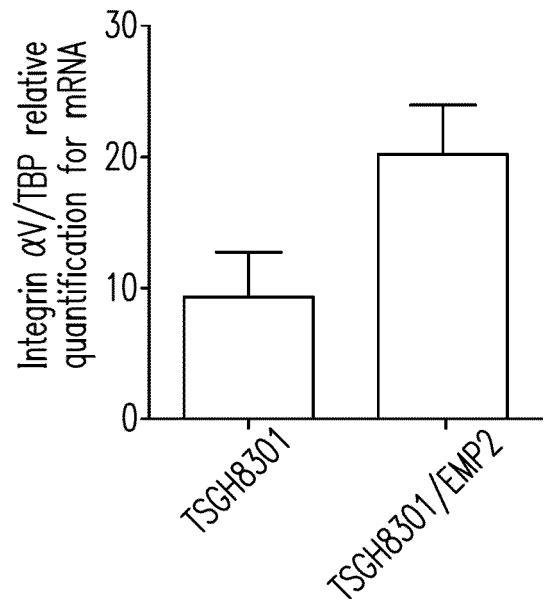
FIGS. 10A and 10B show the quantifications of mRNA expression of TATA-binding protein (TBP) and $\alpha V$ and $\beta 3$ integrins, respectively, in TSGH8301 and TSGH8301/EMP2-2 cells by real-time PCR.
Figure 10B:
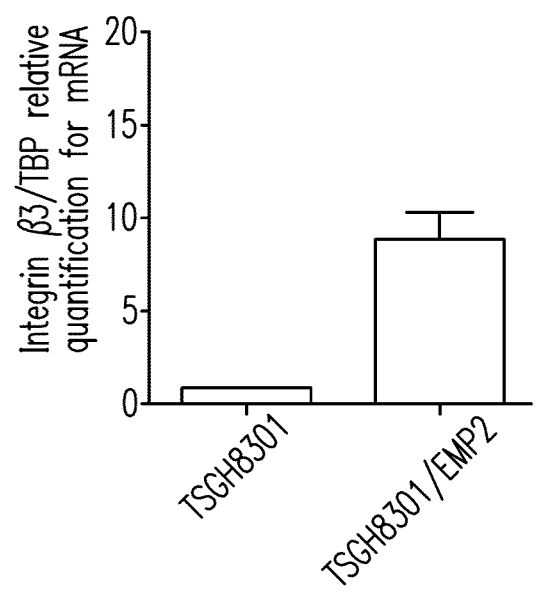

Please refer to FIGS. 10A and 10B. FIGS. 10A and 10B show the quantifications of mRNA expression of TATA-binding protein (TBP) and αV and β3 integrins, respectively, in TSGH8301 (TSGH8301 column) and TSGH8301/EMP2-2 (TSGH8301/EMP2 column) cells by real-time PCR. As shown in FIGS. 10A and 10B, mRNA expression of αV and β3 integrins in TSGH8301/EMP2-2 cell line is higher than that of TSGH8301 cells, suggesting that mRNA expression of αV and β3 integrins is increased with EMP2 over-expression. Moreover, it is known that regulators and/or factors up-regulate the expression of EMP2 can enhance the expressions of α1 and α5 integrins.

Based on observations above, either isoflavone or EMP2 over-expressed plasmid can be the regulator and/or factor to up-regulate the expression of EMP2. Over-expression of EMP2 can not only inhibit the growth of cancer cell, but also increase the expressions of integrins. That is, if there is a disease having to be treated via increased expression of integrins in cell and/or in tissue, the regulator and/or factor, e.g. isoflavone or EMP2 over-expressed plasmid, can be applied to enhance the expression of EMP2 so as to up-regulate the expression of integrins. For example, integrins promote nerve growth. Accordingly, the regulator and/or factor for increasing the expression of EMP2 may be used for the promotion of repair and/or regeneration of central nervous system. That is, regulator and/or factor(s) up-regulate the expressions of integrins can be used to treat a partially or totally disabled nervous injury by the promotion of repair or regeneration of the nerve.

RNA interference targeting on EMP2 and integrins was also used for confirmation of the relationship between EMP2 expression and integrins.

Figure 11:
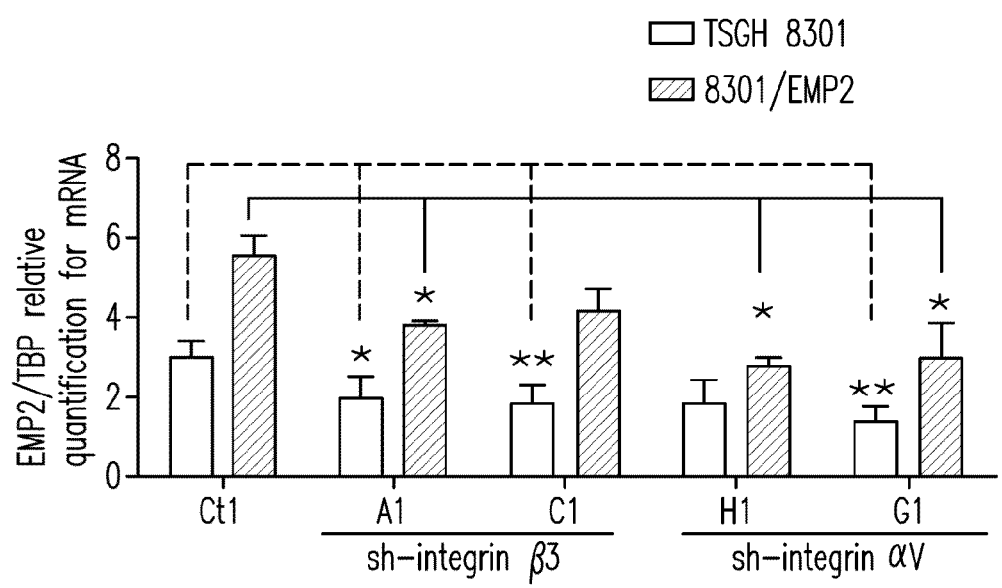
FIG. 11 shows the quantifications of mRNA expression of EMP2 and TBP in TSGH8301 and TSGH8301/EMP2-2 cell lines.

FIG. 11 shows the quantifications of mRNA expression of EMP2 and TBP in TSGH8301 and TSGH8301/EMP2-2 cell lines. These two cell lines were transfected with small hairpin RNAs (shRNA) against αV and β3 integrins, respectively. In brief, TSGH8301 and TSGH8301/EMP2-2 cell lines were transfected with shRNAs of A1 or C1 against β3 integrin, shRNAs of H1 or G1 against αV integrin. The mRNA of EMP2 and TBP of these transfected cell lines were harvested for quantification by real-time PCR. The sequences of shRNAs of A1 (SEQ ID NO. 1), C1 (SEQ ID NO. 2), H1 (SEQ ID NO. 3) and G1 (SEQ ID NO. 4) are 5'-CCGGCATTATGTT-TACAGAGGACAACTCGAGTTGTCCTCTGTAAACAT-AATGTTTTT-3', 5'-CCGGCCCTGTTACAATATGAA-GAATCTCGAGATTCTTCATATTGTAACAGGGTTTTT-3', 5'-CCGGGCCTTACAAATACAACAACAACTCGAG-TTGTTGTTGTATTTGTAAGGCTTTTTG-3' and 5'-CCG-GCGAGGGAAGTTACTTCGGATTCTCGAGAATCCGA-AGTAACTTCCCTCGTTTTTG-3', respectively. After transfections of shRNAs of A1, C1, H1 and G1, expressions of αV and β3 integrins in TSGH8301 and TSGH8301/EMP2-2 cell lines were repressed correspondingly. Besides, mRNA expression of EMP2 and TBP in TSGH8301 and TSGH8301/EMP2-2 cell lines without transfection was taken as controls (Ctl).

As shown in FIG. 11, after transfections of shRNAs against αV and β3 integrins, mRNA expression of EMP2 in either TSGH8301 or TSGH8301/EMP2-2 cell lines is significantly suppressed (**P<0.001 and *P<0.05, paired Student's t test), supporting that inhibition of integrins suppresses the expression of EMP2. Thus, inhibitor, such as shRNAs, of integrins expression can also inhibit the expression of EMP2.

Figure 12A:
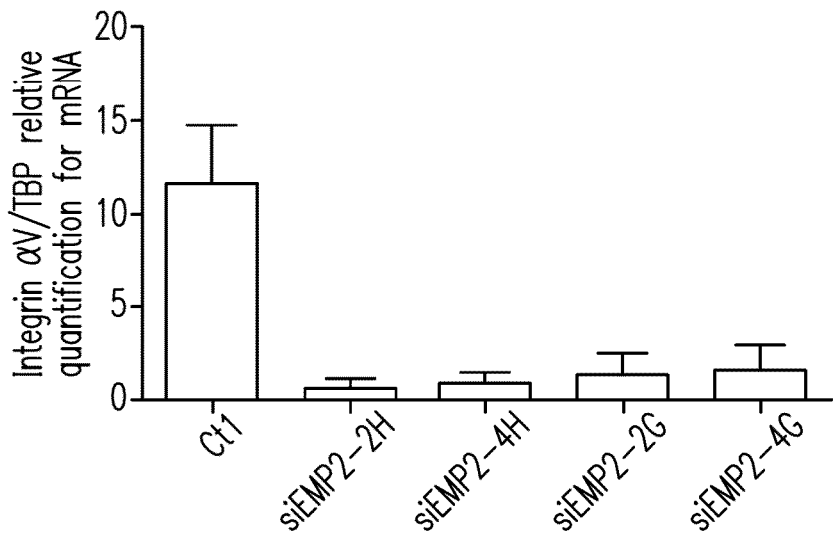
FIGS. 12A and 12B show the quantifications of mRNA expression of TBP and αV and β3 integrins in TSGH8301 cell line being transfected with small interfering RNA (siRNA) against EMP2.
Figure 12B:
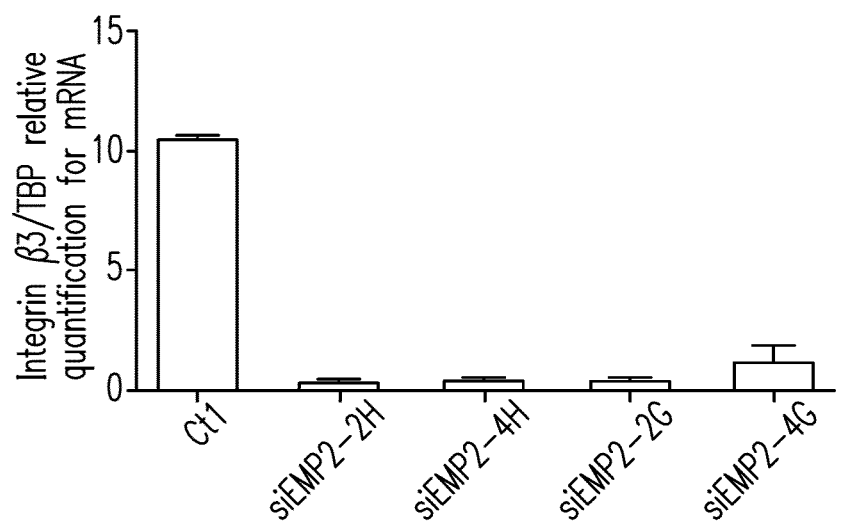

Both FIGS. 12A and 12B show the quantification of mRNA expression of TBP and αV and β3 integrins in TSGH8301 cell line being transfected with small interfering RNA (siRNA) against EMP2. Specifically, TSGH8301 cell line was transfected with siRNAs of si-EMP2-2H, si-EMP2-4H, si-EMP2-2G and si-EMP2-2G, respectively. The mRNA of αV and β3 integrins of these transfected cell lines were harvested for real-time PCR analysis. After transfection of siRNAs of si-EMP2-2H, si-EMP2-4H, si-EMP2-2G or si-EMP2-2G, respectively, expression of EMP2 in TSGH8301 cell line is inhibited correspondingly. Besides, mRNA expressions of TBP and αV and β3 integrins of TSGH8301 cell line without transfection were taken as the controls (Ctl) as shown in FIGS. 12A and 12B.

As shown in FIGS. 12A and 12B, after transfection with siRNA against EMP2, mRNA expressions of αV and β3 integrins in TSGH8301 cell line were significantly inhibited (P<0.05 and P<0.001, respectively, one-way ANOVA), supporting that inhibition of EMP2 expression suppresses the expression of integrins. Thus, inhibitor, such as siRNA, of the EMP2 expression can also inhibit the expression of integrins.

Moreover, when cells were transfected with siRNA against EMP2, expressions of both EMP2 and integrins are inhibited. Accordingly, if there is a disease having to be treated via suppression of integrins in cell and/or in tissue, regulator and/or factor, e.g. siRNA against EMP2, to inhibit the expression of EMP2 can be applied to reduce the expressions of integrins. For example, some diseases, including cancer, multiple sclerosis, Crohn's disease, psoriasis, rheumatoid arthritis, and acute coronary syndromes, may be treated by inhibiting the expression of integrins, i.e. treated with inhibitor of EMP2.

On the other hand, TSGH8301 is a human bladder cancer cell line, and regulation of expression of integrins in TSGH8301 is achievable by regulation of EMP2 expression as above-mentioned. That is, compared with previous studies and clinical application of EMP2 that are limited in the diseases related to pathway regulated by female hormones, the above-mentioned Figs. and descriptions demonstrate that expression of integrins can be regulated by EMP2 expression in bladder cancer mode, which is unrelated to pathways regulated by female hormones.

Moreover, none of the above-mentioned isoflavone, EMP2 over-expressed plasmid and siRNA against EMP2 is the regulator triggering EMP2 expression via antagonism. Thus, the above-mentioned regulators of EMP2 are non-antagonistic ones, and can be used for modulation of EMP2 expression in the activation of integrins without involvement of female hormones.

In conclusion, the present disclosure demonstrates that isoflavonoids up-regulate the expression of EMP2. Besides, expression of EMP2 could be activated via gene transfection and EMP2 and integrins are co-expressed and co-regulated as supported by RNAi experiments. With modulation of EMP2 expression, expression of integrins is also altered in the same direction. Accordingly, regulation of EMP2 expression is an effective tool for management the expressions of integrins.

Therefore, via non-antibody method, such as isoflavonoids treatment, gene transfection and RNAi, EMP2 expression is regulated therefore further control the expressions of integrins, resulting in clinical improvement of human diseases.

Moreover, the present disclosure shows that isoflavonoids up-regulate the expression of EMP2, and over-expressed EMP2 inhibits the growth of bladder cancer. Among patients with upper urinary tract carcinoma, those with over-expressed EMP2 primary tumors have a higher survival rate after the surgical resection than those with lower or no expression of EMP2 in their tumors. Accordingly, the present disclosure also reveals a regulator in regulating the expressions of EMP2 and integrins and being applied to treatment of bladder cancer.

The present disclosure establishes the relationship between the EMP2 and integrins r. Based on this, it is discovered that regulator of EMP2 expression can be the ingredient of pharmaceutical composition in the treatment of integrin-associated diseases. It is also unveiled that regulator of expressions of integrins can be the ingredient of pharmaceutical composition in the treatment of EMP2-associated diseases.

EMBODIMENTS

Embodiment 1: A method for treating integrin-associated disease in a mammal, comprising a step of administrating to the mammal an effective amount of a regulator modulating the expression of epithelial membrane protein 2 (EMP2).

Embodiment 2 is a method as described in Embodiment 1, wherein the regulator is at least one of isoflavones and a plasmid over-expressing the EMP2, the regulator enhances the expression of both EMP2 and integrins, and the disease needs to be treated via an increased expression of integrins.

Embodiment 3 is a method as described in Embodiment 1 or 2, wherein the isoflavone is a genistein.

Embodiment 4 is a method as described in Embodiments 1 to 3, wherein the integrins are selected from the group consisting of an αV integrin, an α6 integrin, a β3 integrin, a β6 integrin, αVβ3 integrins and a combination thereof.

Embodiment 5 is a method as described in Embodiment 1 to 4, wherein the integrin-associated disease is a nervous injury and the increased expression of integrins promotes a repair or a regeneration of nerve.

Embodiment 6 is a method as described in Embodiments 1 to 5, wherein the nerve is partially or totally disabled.

Embodiment 7 is a method as described in Embodiment 1, wherein the regulator is an inhibitor of EMP2, the regulator inhibits the expression of both EMP2 and integrins, and the integrin-associated disease is one selected from the group consisting of a cancer, a multiple sclerosis, a Crohn's disease, a psoriasis, a rheumatoid arthritis, acute coronary syndromes and a combination thereof.

Embodiment 8 is a method as described in Embodiment 7, wherein the inhibitor is one selected from the group consisting of a siRNA against EMP2, a shRNA against EMP2, a shRNA against αV integrin, a shRNA against β3 integrin and a combination thereof.

Embodiment 9 is a method as described in any of Embodiments 1 to 8, wherein the integrin-associated disease is one selected from the group consisting of an αV integrin-associated disease, a β3 integrin-associated disease, an αVβ3 integrins-associated disease and a combination thereof.

Embodiment 10 is a method as described in any of Embodiments 1 to 9, wherein the expression of EMP2 is at mRNA level.

Embodiment 11: A method for treating epithelial membrane protein 2 (EMP2)-associated disease in a mammal, comprising a step of administrating to the mammal an effective amount of inhibitor suppressing the expression of integrins.

Embodiment 12 is a method as described in Embodiment 11, wherein the integrin is one selected from the group consisting of an αV integrin, a β3 integrin, αVβ3 integrins and a combination thereof.

Embodiment 13 is a method as described in Embodiment 11 or 12, wherein the inhibitor is one selected from the group consisting of a siRNA, a shRNA and a combination thereof, and both the siRNA and shRNA are against the integrins.

Embodiment 14 is a method as described in any of Embodiments 11 to 13, wherein EMP2-associated disease is one selected from the group consisting of a cancer, a multiple sclerosis, a Crohn's disease, a psoriasis, a rheumatoid arthritis, acute coronary syndromes and a combination thereof.

Embodiment 15 is a method as described in any of Embodiments 11 to 14, wherein the inhibitor suppresses the expression of integrins via a pathway not regulated by female hormones.

Embodiment 16 is a method as described in any of Embodiments 11 to 15, wherein expression of integrins is at mRNA level.

Embodiment 17: A method for treating bladder cancer in a mammal, comprising a step of administrating to the mammal an effective amount of regulator modulating expression of epithelial membrane protein 2 (EMP2) and integrins.

Embodiment 18 is a method as described in Embodiment 17, wherein the integrin is one selected from the group consisting of an α1 integrin, an α5 integrin, an αV integrin, a β3 integrin, αVβ33 integrins and a combination thereof.

Embodiment 19 is a method as described in Embodiment 18 or 19, wherein the regulator up-regulates the expression of EMP2.

Embodiment 20 is a method as described in any of Embodiments 17 to 19, wherein the regulator suppresses at least one a growth and a development of bladder cancer.

While the disclosure has been described in terms of what is presently considered to be the most practical and preferred embodiments, it is to be understood that the disclosure is not limited to the disclosed embodiments. Therefore, it is intended to cover various modifications and similar arrangements included within the spirit and scope of the appended claims, which are to be accorded with the broadest interpretation so as to encompass all such modifications and similar structures.

What is claimed is:

1. A method for treating bladder cancer in a mammal, comprising a step of administering to the mammal an effective amount of one of a first regulator and a second regulator, wherein the first regulator up-regulates an expression of an integrin to up-regulate an expression of an epithelial membrane protein 2 (EMP2), and the second regulator inhibits the expression of the integrin to inhibit the expression of the epithelial membrane protein 2 (EMP2).

2. The method as claimed in claim 1, wherein the first regulator is an isoflavone, the first regulator up-regulates the expression of the integrin, and the disease needs to be treated via the up-regulated expression of the integrin.

3. The method as claimed in claim 2, wherein the isoflavone is a genistein.

4. The method as claimed in claim 2, wherein the integrin is one selected from the group consisting of an αV integrin, an α6 integrin, a β3 integrin, a β6 integrin, αVβ3 integrins and a combination thereof.

5. The method as claimed in claim 1, wherein the second regulator is one selected from the group consisting of an shRNA against an αV integrin, an shRNA against a β3 integrin and a combination thereof.

6. The method as claimed in claim 1, wherein the integrin-associated disease is one selected from the group consisting of an αV integrin-associate disease, a β3 integrin-associated disease, an αVβ3 integrins-associated disease and a combination thereof.

7. The method as claimed in claim 1, wherein the expression of the EMP2 is at an mRNA level.

* * * * *

SEQUENCE LISTING

<160> NUMBER OF SEQ ID NOS: 4

<210> SEQ ID NO 1
<211> LENGTH: 57
<212> TYPE: DNA
<213> ORGANISM: Artificial Sequence

```
<220> FEATURE:
<221> NAME/KEY: misc_RNA
<223> OTHER INFORMATION: Small hairpin RNA (shRNA)

<400> SEQUENCE: 1
ccggcattat gtttacagag dacaactcga gttgtcctct gtaaacataa tgttttt         57

<210> SEQ ID NO 2
<211> LENGTH: 57
<212> TYPE: DNA
<213> ORGANISM: Artificial Sequence
<220> FEATURE:
<221> NAME/KEY: misc_RNA
<223> OTHER INFORMATION: Small hairpin RNA (shRNA)

<400> SEQUENCE: 2
ccggccctgt tacaatatga agaatctcga gattcttcat attgtaacag ggttttt         57

<210> SEQ ID NO 3
<211> LENGTH: 58
<212> TYPE: DNA
<213> ORGANISM: Artificial Sequence
<220> FEATURE:
<221> NAME/KEY: misc_RNA
<223> OTHER INFORMATION: Small hairpin RNA (shRNA)

<400> SEQUENCE: 3
ccgggcctta caaatacaac aacaactcga gttgttgttg tatttgtaag gcttttg         58

<210> SEQ ID NO 4
<211> LENGTH: 58
<212> TYPE: DNA
<213> ORGANISM: Artificial Sequence
<220> FEATURE:
<221> NAME/KEY: misc_RNA
<223> OTHER INFORMATION: Small hairpin RNA (shRNA)

<400> SEQUENCE: 4
ccggcgaggg aagttacttc ggattctcga gaatccgaag taacttccct cgttttg         58
```